(12) United States Patent
Nahabedian

(10) Patent No.: US 7,520,281 B1
(45) Date of Patent: Apr. 21, 2009

(54) FIXED THERAPEUTIC ORAL APPLIANCE

(75) Inventor: Lionel Nahabedian, Los Angeles, CA (US)

(73) Assignee: Group 3 Solutions, L.L.C., Seattle, WA (US)

( * ) Notice: Subject to any disclaimer, the term of this patent is extended or adjusted under 35 U.S.C. 154(b) by 870 days.

(21) Appl. No.: 10/888,850

(22) Filed: Jul. 12, 2004

Related U.S. Application Data

(60) Provisional application No. 60/568,163, filed on May 6, 2004.

(51) Int. Cl.
*A61C 5/14* (2006.01)
*A61C 3/00* (2006.01)
*A61C 19/04* (2006.01)

(52) U.S. Cl. ............ 128/848; 128/859; 128/861; 433/6; 433/68; 433/69; 602/902

(58) Field of Classification Search ........... 128/848, 128/859–862; 602/902; 433/6, 68–69, 215
See application file for complete search history.

(56) References Cited

U.S. PATENT DOCUMENTS

| | | | | |
|---|---|---|---|---|
| 5,365,945 | A * | 11/1994 | Halstrom | 128/848 |
| 5,816,799 | A | 10/1998 | Parker | |
| 5,823,194 | A * | 10/1998 | Lampert | 128/848 |
| 5,829,441 | A * | 11/1998 | Kidd et al. | 128/848 |
| 5,846,212 | A * | 12/1998 | Beeuwkes et al. | 601/38 |
| 5,868,138 | A * | 2/1999 | Halstrom | 128/848 |
| 6,041,784 | A * | 3/2000 | Halstrom | 128/848 |
| 6,161,542 | A * | 12/2000 | Halstrom | 128/848 |
| 6,729,335 | B1 * | 5/2004 | Halstrom | 128/848 |
| 6,769,910 | B1 * | 8/2004 | Pantino | 433/6 |
| 6,845,774 | B2 * | 1/2005 | Gaskell | 128/848 |

OTHER PUBLICATIONS

ADSM Dialogue magazine, Fall, 2002, pp. 11-12, US.
TAP product description, 2 pages,US. Product described in printed pub., in public use, on sale, and/or known or used by others in US since at least Mar. 14, 2000.
Silent Nite product description, 2 pages, US. Product described in printed pub., in public use, on sale, and/or known or used by others in US since at least Mar. 14, 2000.
Klearway Appliance product description, 3 pages,US. Product described in printed pub., in public use, on sale, and/or known or used by others in US since at least Mar. 14, 2000.
Silencer System product description, 2 pages, US. Product described in printed pub., in public use, on sale, and/or known or used by others in US since at least Mar. 14, 2000.

* cited by examiner

*Primary Examiner*—Patricia Bianco
*Assistant Examiner*—Brandon Jackson
(74) *Attorney, Agent, or Firm*—Gregory W. Moravan

(57) ABSTRACT

An oral appliance having upper and lower channel elements attached, respectively, to upper and lower bite blocks. The two channel elements are oriented at a right angle with respect to each other. One of the channel elements carries a removable insert having an array of adjustment holes. A removable coupling member has a support rod with an anchor piece and anchor pin at one of its ends. The anchor piece is received by the channel element carrying the insert, while the anchor pin is received by one of the insert's adjustment holes. A base at the other end of the support rod is received by the other channel element, so that the coupling member may releasably connect the two channel elements together.

17 Claims, 1 Drawing Sheet

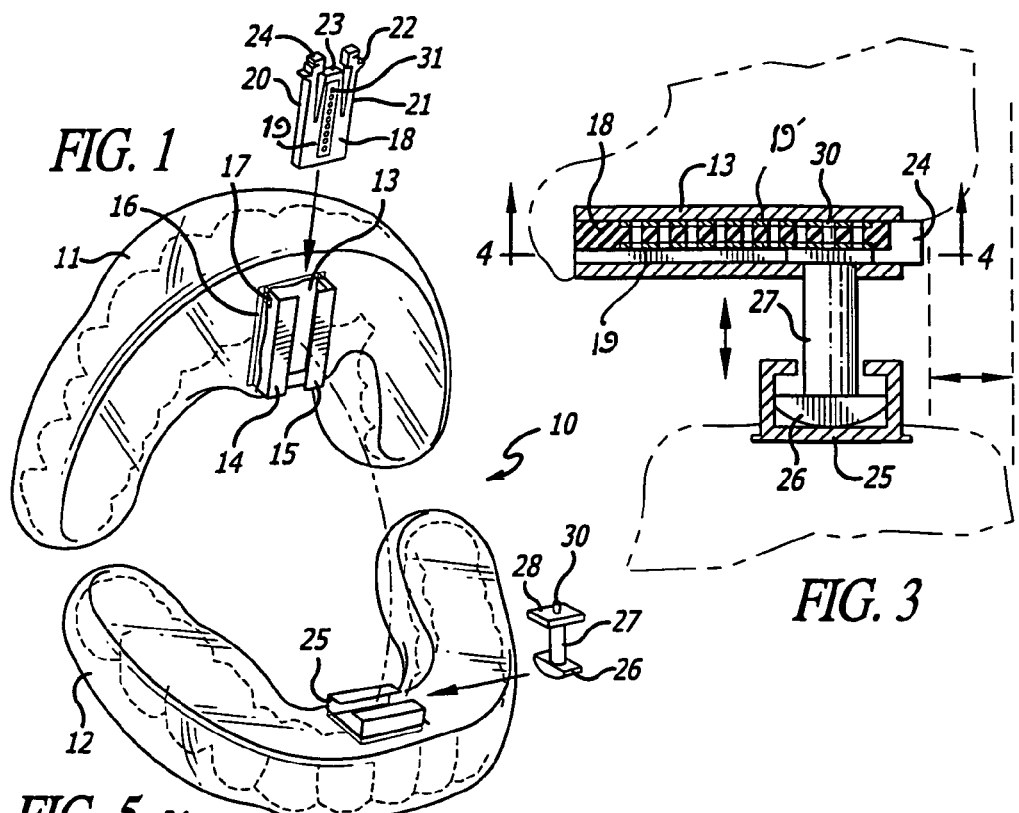
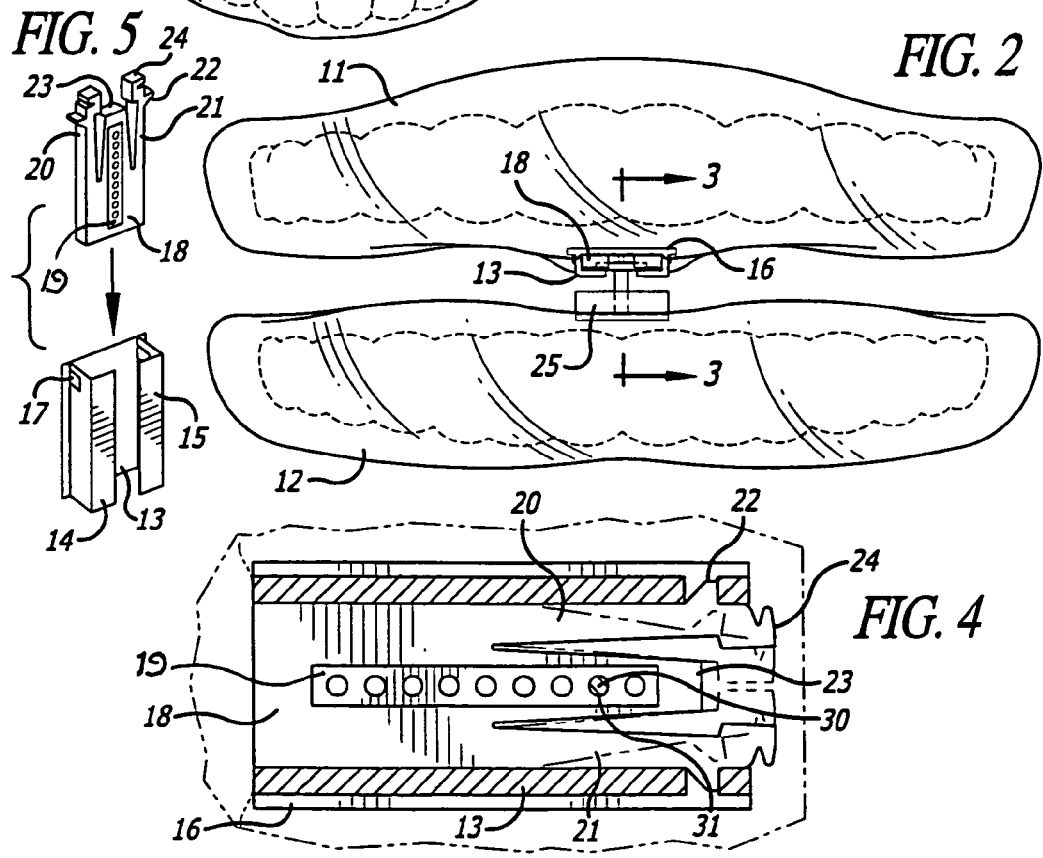

FIXED THERAPEUTIC ORAL APPLIANCE

Priority Claimed on Ser. No. 60/568,163 filed May 6, 2004 PENDING

BACKGROUND OF THE INVENTION

1. Field of the Invention

The present invention relates to the field of dental appliances, and more particularly to a sleep apnea appliance for adjustably positioning the user's lower jaw into a forward position and for increasing the vertical dimensions of the user's mouth for opening the user's airway for easier breathing.

2. Brief Description of the Prior Art

In the past, it has been the conventional practice to provide a dental appliance to be worn by a user at night for treatment of snoring and obstructive sleep apnea. The appliance generally consists of an upper bite block conforming to the user's maxillary dentition, a lower bite block conforming to the user's mandibular dentition, and a connecting assembly secured to an anterior region of the upper and lower bite blocks for adjustably coupling the upper and lower bite blocks together.

Problems and difficulties have been encountered with such conventional dental appliances which stem largely from the fact that a multiplicity of parts and elements are necessary in order to mount, connect and use the above mentioned assembly. Such conventional assemblies employ side-bars, clasps, wires and screw mechanisms which are complicated to assemble and require constant maintenance. Most of the conventional dental appliances do not allow for various vertical settings, nor do they allow for lateral movement for the lower jaw, as well as allowing for anterior and posterior adjustability. An example of a conventional dental appliance which suffers from the problems and difficulties is represented in the disclosures of U.S. Pat. No. 6,041,784 and U.S. Pat. No. 6,161,542.

Therefore, a long-standing need has existed to provide a dental appliance which provides for lower jaw positioning into a forward position and which will also increase the vertical opening of a patient's mouth in order to expand the patient's airway. The novel dental appliance should contain no more than four parts that are readily assembled without the necessity for threaded screws and wrenches.

SUMMARY OF THE INVENTION

Accordingly, the above problems and difficulties are avoided by the present invention which provides a dental appliance for the treatment of snoring and/or obstructive sleep apnea which includes an upper thermoplastic transparent member conforming to the user's maxillary dentition, a lower thermoplastic transparent member conforming to the user's mandibular dentition, and which further includes a connecting assembly adjustably securing the upper and lower bite blocks so that the upper and lower bite blocks are releasably coupled together. In one form of the invention, the upper and lower bite blocks include a pair of channel elements, each having an elongated slot, which are arranged perpendicular to each other, and wherein the upper bite block includes a receptacle for insertably receiving an insert having flexible nubs and tabs that releasably connect with the anterior portion of the upper bite channel element. The lower channel element insertably receives and slidably retains a coupling element comprising a base with an upright support secured to an anchor piece having a pin projecting therefrom. The base is insertably received within the interior of the lower channel element so that the support slides through the slot. The anchor piece carried on the support is engageable with the upper channel element so that the outwardly projecting pin carried on the anchor piece can be inserted into a selected one of a plurality of holes in the insert. The selection of the hole in the insert adjusts the relative position between the upper and lower thermoplastic transparent members. It is to be noted that the insert is detachably connectable with the upper channel element and that the flexible arms of the insert can be flexed to engage and disengage a nub with openings in the sides of the upper channel element. Tabs at the distal end of each flexible arm serve to close the opening at the end of the upper channel member when the insert fully occupies the channel therein and when the nubs are expanded outwardly to engage with the respective openings.

Therefore, it is among the primary objects of the present invention to provide a dental appliance which positions the lower jaw into a forward position and which can increase the vertical opening of the patient's mouth to provide an open airway.

Another object of the present invention is to provide a dental appliance which is manufactured employing titanium alloy and wherein the titanium assembly is attached to a transparent thermoplastic member adapted to fit both oral arches.

Still another object of the present invention is to provide a novel dental appliance which will open the patient's airway without interfering with breathing through the mouth and which contains no more than four parts which are readily assembled without the use of screws, wrenches, or special equipment.

A further object resides in a novel dental appliance that provides the sleep apnea professional with all the functional adjustments necessary for the treatment of sleep apnea and snoring therapies.

Still a further object resides in providing a dental appliance which allows for various vertical settings, lateral movement for the lower jaw, and which allows anterior and posterior adjustability.

Another object resides in providing a fixed dental appliance having an insert with adjustment holes surrounded by reinforcement metal film or plates so as to extend longevity of the appliance.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood with reference to the following description, taken in connection with the accompanying drawings in which:

FIG. 1 is an exploded front perspective view illustrating the novel dental appliance incorporating the present invention;

FIG. 2 is a front elevational view of the dental appliance shown in FIG. 1;

FIG. 3 is an enlarged sectional view of the upper bite channel element and retaining pin assembly as used in the embodiment shown in FIGS. 1 and 2 as taken in the direction of arrows 3-3 of FIG. 2;

FIG. 4 is an enlarged top plan sectional view of the upper channel and pin assembly illustrated in FIG. 3 as taken in the direction of arrows 4-4 thereof; and FIG. 5 is a perspective view of the insert and upper channel element as used in the embodiment shown in FIGS. 1 and 2.

DESCRIPTION OF PREFERRED EMBODIMENT

Referring to FIG. 1, the novel fixed dental appliance incorporating the present invention is illustrated in the general direction of arrow 10 which includes an upper and a lower thermoplastic transparent form or member indicated by numerals 11 and 12 respectively. These forms are processed by a laboratory technician so that the members or forms will fit both oral arches when worn by the user. The upper form 11 includes a bite block taking the form of an elongated channel element 13 having a slot defined between the opposing edges of flanges 14 and 15 respectively. The channel includes a base element 16 that is embedded in the thermoplastic material of the form 11. Also, each side of the channel element 13 includes an opening, such as opening 17. The opposite ends of the channel element are open so as to insertably receive an insert 18 which includes a linear line of holes 31 and a pair of flexible arms 20 and 21 on opposite sides and having distal ends which reside on the anterior end of the channel element 13. The insert further includes a pair of nubs, such as nub 22, on the distal end of each flex arm so that when the insert 18 is pushed into the receptacle of channel element 13 the flex arms will move inwardly against a midsection 23 until the nub 22 reaches the opening 17 which would then permit the flex arms to expand and engage the nubs with the sides of the channel element. The extreme end of each flex arm includes a tab 24 which closes off the end of the channel element when the insert is fully occupied within the receptacle of the channel element.

FIG. 1 also illustrates that a lower channel element 25 is embedded in the thermoplastic form or member 12. Both channel elements are of identical construction except that the side of the lower channel element does not include openings 17 as carried on the upper channel element 13. The lower channel element includes an elongated slot which is open-ended in order to receive a coupling member comprising a base 26 having a support rod 27 upwardly projecting therefrom and terminating in an anchor piece 28 that includes an upwardly projecting pin 30. In practice, coupling between the upper and lower forms is established by the coupling member whereby the base 26 is inserted into the open end of lower channel element 25 so that the support rod 27 passes through the slot formed therein. Upon reaching a midsection between the opposite ends of the channel element, the anchor piece 28 is inserted into the open end of the upper channel element 13 whereby the pin 30 is placed for lateral positioning in a selective hole of the plurality of holes, such as hole 31 in the insert. The under-side of the insert includes a recess mounted metal film or plate 19 for reinforcement purposes. An upper film or plate 19 is seen in FIG. 3.

Referring now in detail to FIG. 2, it can be seen that the forms 11 and 12 are coupled together by the coupling means whereby the base 26 is attached to the lower channel element 25 and that the anchor piece 28 is coupled with the upper channel element 13 and that the pin 30 is inserted into a selected one of the holes in the insert 18. It can also be understood in FIG. 2 that the channels in the respective upper and lower channel elements 13 and 25 are perpendicular to one another.

Referring now in detail to FIG. 3, the base 26 of the coupling means is dome-shaped and inserted into the receptacle of the lower channel element 25 while the anchor piece 28 is carried in the opening of upper channel element 18. The tab 24 associated with each of the flex arms 20 and 21 close off the opening end of the upper channel piece. The support rod 27 is slidably carried in the slot of the upper channel element 13 and the insert 18 is within the cavity of the channel element 13. It can be seen that the upwardly projecting pin 30 resides within a selected one of the plurality of metal reinforced holes in the insert so that the coupling means can be adjusted along the length of the insert which adjusts the lower form 12 to a desired jaw position. At least one reinforcement film or plate 19 or 19' may be employed to protect the holes 31.

In FIG. 4, the flexing of arms 20 and 21 are illustrated between solid lines and broken lines so that the nubs 22 can be inserted into or retracted from the openings in the side of the upper channel element 13. Pin 30 is illustrated in the first reinforced hole 31 of the plurality of holes for adjusting the position of the lower form member 12. Metal film or plate 19 surrounds each of the holes. The insert 18 may be removed from the upper channel element by pushing the tabs 24 inwardly so that the flexible arms bear against the midsection 23. At this point, the insert may be removed from the upper channel element. Undercut notches 29 at each tab 24 may receive a fingernail for ease in pulling the tabs together for moving the arms 20 and 21. The broken line position of the flex arms indicates the position whereby the insert can be moved.

Referring now in detail to FIG. 5, it can be seen that the insert 18 may be entered into the channel 13 from either end but preferably from the forward end so that the full length of the insert is within the upper channel element 13 when the nubs 22 engage with the openings 17. Preferably, the insert is composed of a plastic-like material and all of the metal parts which include the upper and lower channel elements as well as the coupling means are composed of a titanium alloy.

Therefore, it can be seen that the present invention is differentiated from the prior art appliances because such conventional appliances employ far more components than the four employed by the present invention. The prior appliances are complicated and require constant maintenance. The transparent thermoplastic forms 11 and 12 fit both oral arches and are prepared by expert laboratory technicians. The upper and lower channel elements are incorporated or embedded into the thermoplastic material and the channels in each of the respective channel elements are normal with respect to each other. The lower channel element accommodates the coupling means and the upwardly projecting pin of the coupling means is inserted into a selected one of a plurality of adjustment holes in the insert. Therefore, the dental appliance of the present invention provides functional features, such as allowing various vertical settings, allowing lateral movement of the lower jaw as well as allowing anterior and posterior adjustability.

The length of support rod 27 may vary and may be provided in three separate pin lengths to provide for proper vertical adjustment of mouth opening.

It is particularly noted that the inventive appliance 10 is installed with settings for vertical positioning and advancement without the necessity of removing the appliance from the patient's mouth. No manual tasks are required such as screws, wrenches or the like. All settings are made as installation settings. The tabs on the insert 18 are self-locking and no posterior support is required. Dislodgement cannot be achieved by itself and requires physical withdrawal. There is not protrusion outside of the patient's mouth.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention

What is claimed is:

1. A fixed dental appliance comprising: an upper member conforming to a patient's maxillary dentition; a lower member conforming to said patient's mandibular dentition;
   a connecting means for releasably coupling said upper member and said lower member together to maintain said lower member in an anterior, protruded position relative to said upper member;
   wherein said connecting means comprises a first element on one of said upper and lower members, a second element on the other of said upper and lower members, and a coupling member having a fixed length; wherein said coupling member comprises a support rod terminating at one end in a non-threaded pin and terminating at an opposite end in a dome-shaped anchor;
   wherein said pin is detachably connectable with said first element; and wherein said anchor is detachably connectable with said second element.

2. The dental appliance defined in claim 1 wherein: said first element comprises a first channel member and an insert;
   wherein said first channel member comprises a first channel that is operable to detachably receive said insert;
   wherein said insert comprises a plurality of holes that are operable to selectively receive said pin; and
   wherein said insert further comprises releasable attachment means for detachably connecting said insert with said first channel member.

3. The dental appliance defined in claim 2 wherein:
   said first channel member comprises a pair of openings; and
   wherein said releasable attachment means comprises a pair of resilient fingers normally biased into engagement with said pair of openings in said first channel member when said insert is detachably connected with said first channel member.

4. The dental appliance defined in claim 3 wherein: said second element comprises a second channel member; wherein said second channel member comprises a second channel that is operable to detachably receive said dome-shaped anchor of said coupling member; and wherein said first channel extends normal to said second channel.

5. The dental appliance defined in claim 2 wherein said insert further comprises a reinforcement strip that is disposed about said holes.

6. The dental appliance defined in claim 2 wherein:
   said first channel member comprises an elongated slot that is operable to accommodate said pin when said pin is selectively received by one of said holes in said insert.

7. The dental appliance defined in claim 3 wherein:
   each of said resilient fingers has a distal end and comprises a nub at said distal end, and wherein each of said nubs is operable to be releasably engaged by a respective one of said openings in said first channel member.

8. The dental appliance defined in claim 4, wherein said second channel member comprises an elongated slot that is operable to accommodate said support rod when said dome-shaped anchor is detachably connected with said second channel member.

9. A fixed dental appliance comprising: an upper member conforming to a patient's maxillary dentition; a lower member conforming to said patient's mandibular dentition;
   a connecting means for releasably coupling said upper member and said lower member together to maintain said lower member in an anterior, protruded position relative to said upper member;
   wherein said connecting means comprises a first element on one of said upper and lower members, a second element on the other of said upper and lower members, and a coupling member having a fixed length; wherein said coupling member comprises a support rod terminating at one end in a non-threaded pin and terminating at an opposite end in an anchor;
   wherein said pin is detachably connectable with said first element; and wherein said anchor is detachably connectable with said second element.

10. The dental appliance defined in claim 9 wherein: said first element comprises a first channel member and an insert;
    wherein said first channel member comprises a first channel that is operable to detachably receive said insert;
    wherein said insert comprises a plurality of holes that are operable to selectively receive said pin; and
    wherein said insert further comprises releasable attachment means for detachably connecting said insert with said first channel member.

11. The dental appliance defined in claim 10 wherein:
    said first channel member comprises a pair of openings; and
    wherein said releasable attachment means comprises a pair of resilient fingers normally biased into engagement with said pair of openings in said first channel member when said insert is detachably connected with said first channel member.

12. The dental appliance defined in claim 11 wherein: said second element comprises a second channel member; wherein said second channel member comprises a second channel that is operable to detachably receive said anchor of said coupling member; and wherein said first channel extends normal to said second channel.

13. The dental appliance defined in claim 10 wherein said insert further comprises a reinforcement strip that is disposed about said holes.

14. The dental appliance defined in claim 10 wherein:
    said first channel member comprises an elongated slot that is operable to accommodate said pin when said pin is selectively received by one of said holes in said insert.

15. The dental appliance defined in claim 11 wherein:
    each of said resilient fingers has a distal end and comprises a nub at said distal end, and wherein each of said nubs is operable to be releasably engaged by a respective one of said openings in said first channel member.

16. The dental appliance defined in claim 12, wherein said second channel member comprises an elongated slot that is operable to accommodate said support rod when said anchor is detachably connected with said second channel member.

17. The dental appliance defined in claim 9, wherein said anchor is dome-shaped.

* * * * *